(12) United States Patent
Paden et al.

(10) Patent No.: US 8,821,135 B2
(45) Date of Patent: Sep. 2, 2014

(54) DEVICES AND SYSTEMS FOR MEDICAL FLUID TREATMENT

(75) Inventors: Matthew L. Paden, Stone Mountain, GA (US); Ajit Yoganathan, Tucker, GA (US); Lakshmi Prasad Dasi, Fort Collins, CO (US)

(73) Assignees: Emory University, Altanta, GA (US); Georgia Tech Research Corporation, Atlanta, GA (US)

( * ) Notice: Subject to any disclaimer, the term of this patent is extended or adjusted under 35 U.S.C. 154(b) by 201 days.

(21) Appl. No.: 13/218,328

(22) Filed: Aug. 25, 2011

(65) Prior Publication Data

US 2012/0048407 A1 Mar. 1, 2012

Related U.S. Application Data

(60) Provisional application No. 61/376,720, filed on Aug. 25, 2010.

(51) Int. Cl.

| F04B 45/047 | (2006.01) |
| F04B 43/09 | (2006.01) |
| A61M 1/10 | (2006.01) |
| F04B 43/02 | (2006.01) |
| A61M 1/34 | (2006.01) |
| A61M 1/16 | (2006.01) |

(52) U.S. Cl.
CPC *F04B 43/02* (2013.01); *A61M 1/34* (2013.01); *A61M 1/1037* (2013.01); *A61M 1/1049* (2014.02); *A61M 1/16* (2013.01)
USPC ....................................................... 417/413.1

(58) Field of Classification Search
CPC .............................. F04B 43/025; F04B 43/02

USPC ......................................... 417/395, 413.1, 571
See application file for complete search history.

(56) References Cited

U.S. PATENT DOCUMENTS

| 2,619,907 A | * | 12/1952 | Paterson ............................ 92/60 |
| 4,468,222 A | * | 8/1984 | Lundquist ...................... 604/153 |
| 5,165,869 A | * | 11/1992 | Reynolds ....................... 417/385 |
| 5,306,510 A | | 4/1994 | Meltzer |
| 5,452,993 A | * | 9/1995 | Lanigan ...................... 417/413.1 |
| 5,836,908 A | | 11/1998 | Beden et al. |
| 6,471,872 B2 | | 10/2002 | Kitaevich et al. |
| 6,638,477 B1 | | 10/2003 | Treu et al. |
| 6,638,478 B1 | | 10/2003 | Treu et al. |
| 6,673,314 B1 | | 1/2004 | Burbank et al. |
| 6,852,090 B2 | | 2/2005 | Burbank et al. |
| 7,112,273 B2 | | 9/2006 | Weigel et al. |

(Continued)

FOREIGN PATENT DOCUMENTS

WO 2008154376 A2 12/2008

*Primary Examiner* — Bryan Lettman
(74) *Attorney, Agent, or Firm* — Emory Patent Group; Randi Beth Isaacs

(57) ABSTRACT

The devices and systems are medical fluid treatment therapies. The device and systems are configured and capable of operating based on small volumes of fluids. The devices and systems include a pump configured for small volume of a fluid. The pump may include a first conduit configured for inflow of the fluid; a second conduit configured for outflow of the fluid; a fluid chamber configured to move the fluid through the pump; a diaphragm configured to force the fluid through the fluid chamber by indirectly exerting force on the fluid chamber; and a connector configured to removably attach the pump to a motor.

20 Claims, 17 Drawing Sheets

(56) References Cited

U.S. PATENT DOCUMENTS

| | | |
|---|---|---|
| 7,267,658 B2 | 9/2007 | Treu et al. |
| 7,351,340 B2 | 4/2008 | Connell et al. |
| 7,517,332 B2 | 4/2009 | Tonelli et al. |
| 7,645,253 B2 | 1/2010 | Gura et al. |
| 7,776,006 B2 | 8/2010 | Childers et al. |
| 2003/0209475 A1* | 11/2003 | Connell et al. ............... 210/143 |
| 2004/0245161 A1 | 12/2004 | Treu et al. |
| 2005/0281809 A1 | 12/2005 | Roberts et al. |
| 2006/0184084 A1 | 8/2006 | Ware et al. |
| 2009/0113335 A1 | 4/2009 | Sandoe et al. |
| 2010/0288703 A1 | 11/2010 | Fortenberry |

* cited by examiner

DEVICES AND SYSTEMS FOR MEDICAL FLUID TREATMENT

CROSS-REFERENCE TO RELATED APPLICATIONS

This application claims priority to U.S. Provisional Application No. 61/376,720 filed Aug. 25, 2010, which is hereby incorporated by reference.

ACKNOWLEDGEMENTS

This invention was made with government support under Grant No. 1RC1DK086939 awarded by National Institute of Diabetes and Digestive and Kidney Diseases National Institutes of Health). The government has certain rights in the invention.

FIELD

This disclosure relates to devices and systems for medical fluid treatment therapies. More particularly, the disclosure relates to devices and systems for extracorporeal blood treatment having accurate fluid management of small volumes.

BACKGROUND

Medical fluid treatment therapies are generally used to treat loss of renal function or renal failure. A person's renal system can fail due to disease, injury or other causes, such as complications associated with extracorporeal membrane oxygenation (ECMO) treatment. During renal failure or loss of renal function, toxic end products of metabolism (e.g., urea, creatinine, uric acid, and others) can accumulate in blood and tissues because the balance of water, minerals and the excretion of daily metabolic load can be reduced or no longer possible.

Renal support can be provided by a continuous renal replacement therapy (CRRT), such as continuous venovenous hemofiltration (CVVH) or continuous venovenous hemodiafiltration (CVVHDF). These therapies are designed to remove metabolic waste and excess fluid from patient in fluid overload and those who need renal support. These therapies allow provide continuous fluid, electrolyte and toxin clearance even in the absence of adequate native renal function via convective or dialytic processes through a permeable membrane.

CRRT is a common renal replacement therapy for critically ill and hemodynamically unstable patients in the pediatric intensive care unit. However, there is currently no FDA approved CRRT device for use in the neonatal and pediatric populations. Generally, physicians resort to utilizing devices approved for adults to treat children. The adult approved CRRT devices are not designed for the smaller volumes inherent in treating children.

SUMMARY

Thus, there is a need for devices capable of handling a smaller fluid volume, such as in the pediatric patient. The disclosure relates to devices and systems for medical fluid treatment. These devices and systems are configured for small fluid volume and allow operating parameters for a small fluid volume.

According to some embodiments, the disclosure may relate to a fluid pump for medical fluid treatment therapies configured for small volumes of a fluid. The pump may include a first conduit configured for inflow of the fluid; a second conduit configured for outflow of the fluid; a fluid chamber configured to move the fluid through the pump; a diaphragm configured to force the fluid through the fluid chamber by indirectly exerting force on the fluid chamber; and a connector configured to removably attach the pump to a motor.

According to some embodiments, the fluid pump may include a piston connected to the diaphragm, the piston configured to linearly move a surface, the diaphragm.

The fluid pump may include a housing, the housing including at least a first section and a second section. The first section may include a cavity filled with an incompressible fluid, the first conduit, the second conduit and the fluid chamber, and the cavity is disposed between the fluid chamber and the diaphragm. According to other embodiments, the diaphragm may be fixedly attached to the housing between the first section and the second section. The diaphragm may also be configured to move between a first position and a second position; the first position corresponding to when a surface of the diaphragm protrudes into the first section and the second position corresponding to when the surface of the diaphragm protrudes into the second section. According to some embodiments, the diaphragm may be configured to transfer force to the incompressible fluid when the diaphragm is in the second position, and the incompressible fluid is configured to move the fluid through the fluid chamber.

According to some embodiments, the second section may include a piston. According to some embodiments, the first section may have an extending surface and the second section has an extending surface, the extending surface of the first section facing the extending surface of the second section. According to further embodiments, the pump may include a cap, the cap including ports configured to connect tubing to the first and second conduits.

According to some embodiments, the disclosure may relate to a medical fluid therapy system. The system may include at least one medical fluid pump, the pump including: a fluid chamber configured to move a fluid through the pump; a diaphragm configured to force the fluid through the fluid chamber by indirectly exerting force on the fluid chamber; a plurality of valves, the valves including at least a first valve and a second valve configured to control the flow of fluid through the fluid pump; a motor; and a controller configured to collectively control the movement of the motor and valves with respect to each other.

According some embodiments, the system may include: a fluid balance system; the fluid balance system including a first pump and a second pump, each pump including the fluid chamber, the rolling diaphragm and the first valve and the second valve; wherein the first pump and second pump are offset of each other.

According to some embodiments, the system may further include a display; the display includes a user interface configured to enter operating parameters to control the system. The user interface may display the operating status of the system. The operating status may include flow rates of the fluid flowing through the pump and the angle of the valve.

According to some embodiments, the system may include at least one pump receiving member, the at least one pump receiving member having an depression configured to receive a portion of the pump, wherein the pump includes a housing, the housing including at least a first section and a second section, wherein the first section has an extending surface and the second section has an extending surface, the extending surface of the first section facing the extending surface of the second section, and wherein the depression is configured to receive the extending surface of at least the second section.

According to some embodiments, the system may include at least first and second self-contained sections, wherein the first section includes the controller; and the second section includes the pump receiving member. The system may also be configured for a plurality of fluid treatment modes. The controller may be configured to control the motor and valves based on entered volume parameters or selected treatment modes. According to some embodiments, an operating status of the system may be stored at predetermined intervals.

According to some embodiments, the system may be configured to be connected to another medical fluid treatment therapy device. In some embodiments, the controller may control the system based on the other medical fluid treatment therapy or extracorporeal treatment systems and devices. The other medical fluid treatment device may include at least one of an ECMO device, cardiopulmonary bypass device, ventricular assist device, plasma exchange device, apheresis device, or hemoperfusion device. According to some embodiments, the controller may control the system based on a selected mode, connected therapy device, adjunct therapy, patient type, or any combination thereof. The controller may control at least one operating parameter based on the selected mode, connected therapy device, adjunct therapy, patient type, or any combination thereof.

According to other embodiments, the disclosure may relate to a disposable kit for a medical therapy system. The disposable kit may include a first conduit configured for inflow of the fluid; a second conduit configured for outflow of the fluid; a fluid chamber configured to move the fluid through the pump; a diaphragm configured to force the fluid through the fluid chamber by indirectly exerting force on the fluid chamber; and a connector configured to removably attach the pump to a motor.

In some embodiments, the kit may include tubing configured for the medical therapy system.

DESCRIPTION OF FIGURES

The disclosure can be better understood with the reference to the following drawings and description. The components in the figures are not necessarily to scale, emphasis being placed upon illustrating the principles of the disclosure.

DESCRIPTION OF EMBODIMENTS

Figure 1:
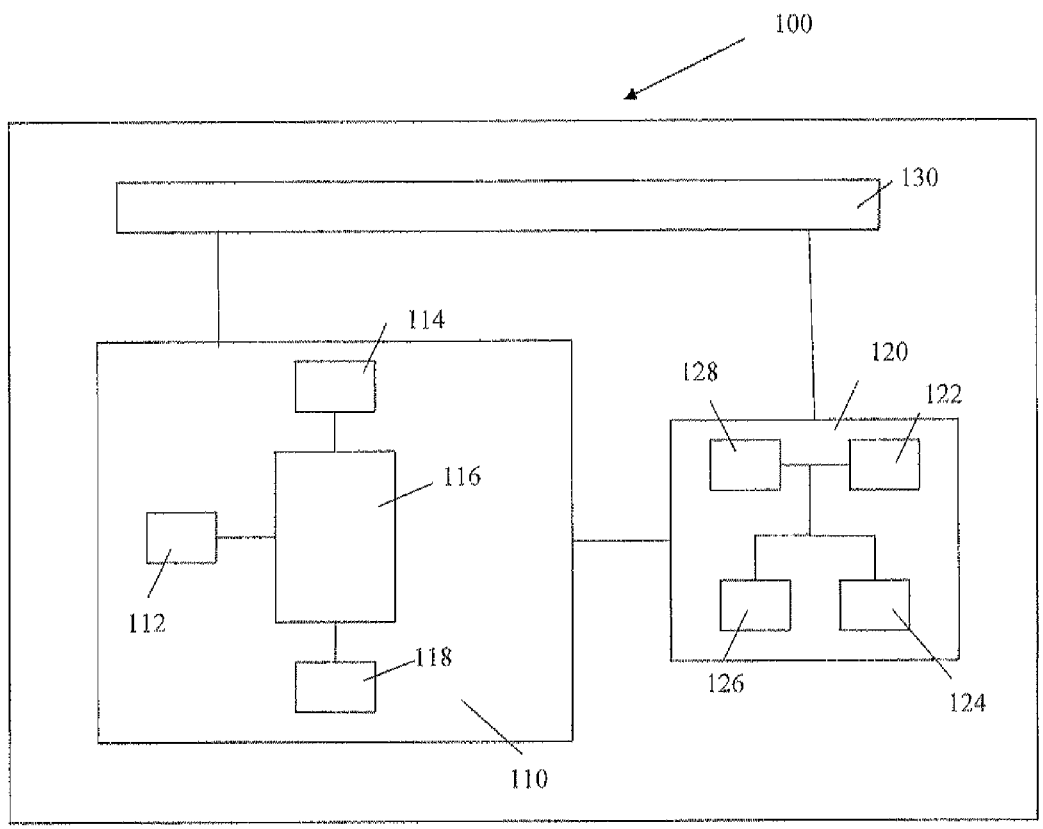
FIG. 1 is a schematic diagram of a medical fluid treatment system according to some embodiments.

The following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

The disclosure relates to devices and systems for medical fluid treatment therapies, such as extracorporeal treatment therapies, to assist patients with severe organ deficiencies. The extracorporeal treatments may include but are not limited to CRRT, CVVH, CVVHD, and CVVHDF. It will be understood that components (such as the blood pump) of the devices and systems, as well as the devices and systems in their entirety, may be implemented into and/or with other medical fluid treatment therapy or extracorporeal treatment systems and devices. According to embodiments, the system may automatically adjust the operation in accordance with the other medical fluid treatment therapy or extracorporeal treatment systems and devices. These other devices may include but are not limited to an ECMO device, cardiopulmonary bypass device, ventricular assist device, plasma exchange device, apheresis device, or hemoperfusion device.

According to embodiments, the disclosure may relate to medical fluid treatment devices and systems capable of small volume fluid management. In some embodiments, the medical fluid treatment devices and systems may provide to CRRT therapy. In some embodiments, the medical fluid treatment devices and systems may be capable of CVVH therapy. In other embodiments, the medical fluid treatment devices and systems may be capable of CVVHDF therapy. In other embodiments, the medical fluid treatment devices and systems may be capable of CVVHD therapy. In further embodiments, medical fluid treatment devices and systems may be capable of providing all CVVH therapy, CVVHD therapy, and CVVHDF therapy.

Systems and Devices

In some embodiments, the systems and devices may include a modular fluid therapy system. FIG. 1 shows an example of a schematic of a system 100 according to some embodiments.

In some embodiments, the system 100 may include a medical fluid therapy system 110. The system 110 may include a plurality of sensors and/or detectors 112. In some embodiments, the sensors 112 may include but are not limited to fluid sensors, temperature sensors, and operation sensors and detectors. The systems may also include additional sensors not shown or described below.

According some embodiments, the fluid sensors configured to detect or measure the fluid characteristics of a fluid along the flow paths. The fluid characteristics include but are not limited to pressure of a fluid flowing through a path, the flow characteristics of the fluid flowing through a path, such as flow rate, the volume of the fluid passing through a path, or combination thereof. The fluid sensors may include but are not limited to a flow meter, a pressure sensor, a volume sensor, or a combination thereof. It will be understood that the fluid sensors described with respect to the systems may be of the same or different type. The sensors may be of any known sensors. The fluid sensors may be disposed within the system to detect or measure the fluid characteristics of the blood flowing through the system including but are not limited to the blood entering the system and exiting the patient, the blood entering the hemofilter, and the blood exiting the system and entering the patient. The fluid sensors may also be disposed within the system to detect or measure the fluid characteristics of the ultrafiltrate, replacement fluid, or dialysate flowing through the system including but are not limited to the ultrafiltrate or used dialysate exiting the hemofilter and/or collected, the replacement fluid exiting the system and entering the patient, and the dialysate entering the hemofilter.

In further embodiments, the sensors 112 may further include at least sensor and/or detector configured to determine/detect the temperature of the fluid flowing through the system. The sensor and/or detector may be any known temperature sensor. The sensor and/or detector may be in combination with a heater.

According to some embodiments, the sensors 112 may include at least one sensor and/or detectors that may be used to determine the operation status of the system. The sensors and/or detectors may provide feedback of the systems and devices according to the embodiments. The sensor and/or detector may be any known detector. The detectors may be configured to detect the presence of certain fluids, for example, the presence of blood, ultrafiltrate, or air.

In some embodiments, the system 110 may include at least one pump configuration 114. According to some embodiments, the pump configuration may include at least one pump and a corresponding valve. The valves may be configured to control the fluid direction through the systems. In some embodiments, the valves may be controlled electronically. In other embodiments, the valves may be controlled mechanically. The valves may include but are not limited to pinch valves. The pinch valves may be made of a sterile, biocompatible material such as polished acrylic. The valves are further described below with respect to the figures. In further embodiments, the pump configurations 114 may include a plurality of fluid pumps along the paths. The fluid pumps may be configured or structured to pump a small volume of fluid. The pumps may be controlled collectively with the valves to move the fluid by a controller. In some embodiments, the pump configurations 114 may include a motor to actuate the pump.

The system 110 may further include at least one controller 116 configured to control the sensors 112 and pump configuration 114. According to some embodiments, the system 110 may include a plurality of controllers. The system 110 may include a main controller and a separate controller for each motor provided for the pump configuration 114. In other embodiments, the system 110 may include a separate controller for each motor provided for the pump configuration 114.

According to some embodiments, the controller may be a CPU. The CPU may be any known may be one or more of any known central processing unit, including but not limited to a processor, or a microprocessor. The CPU may be coupled directly or indirectly to memory elements. The memory 118 may include random access memory (RAM), read only memory (ROM), disk drive, tape drive, etc., or a combinations thereof. The memory may also include a frame buffer for storing image data arrays. The operating status detected by the sensors and/or detectors 112 may be stored in the memory 118. The processes of the system (described below) maybe implemented as a routine that is stored in the memory 118.

Figure 17:
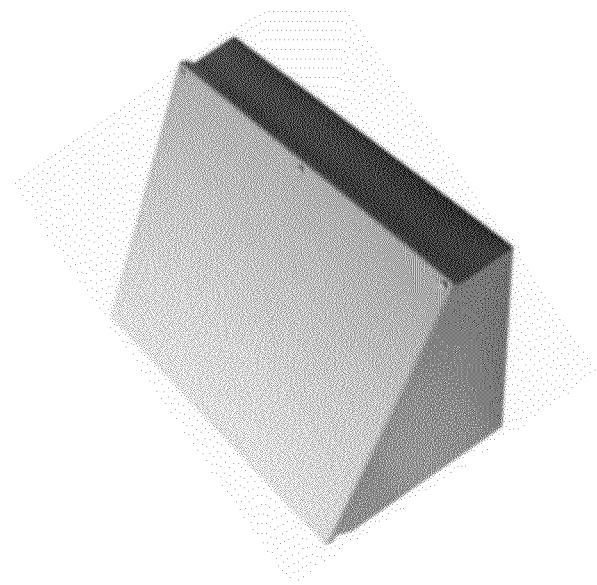
FIGS. 17 and 18 are examples of the modular system according to some embodiments.
Figure 18:

According to some embodiments, the system 100 may further include display system 120. In some embodiments, the display system 120 may be integrated with the medical fluid therapy system 110. In other embodiments, the display system 120 may be separately connectable to the medical fluid therapy system 110. FIGS. 17 and 18 show examples of a system having an integrated modular configuration and/or a separate display unit.

In some embodiments, the display system 120 may include an input device 122 and a display device 124. In some embodiments, the input device 122 may include but is not limited to a touch screen interface, a keyboard, a mouse and trackball. The display device may be any known display device.

In further embodiments, the display device 120 may optionally include a controller 126 and a memory 128. According to some embodiments where the display system 120 may be integrated with the medical fluid therapy system 110, the display system 120 and the medical fluid therapy system 110 may share at least one controller and memory. In further embodiments, the display system 120 may include a separate controller and memory.

According to some embodiments, the controller 126 may be a CPU. The CPU may be any known may be one or more of any known central processing unit, including but not limited to a processor, or a microprocessor. The CPU may be coupled directly or indirectly to memory elements. The memory 128 may include random access memory (RAM), read only memory (ROM), disk drive, tape drive, etc., or a combinations thereof. The memory may also include a frame buffer for storing image data arrays. The operating status detected by the sensors and/or detectors 112 may be stored in the memory 128. The processes of the system (described below) maybe implemented as a routine that is stored in the memory 128.

According to further embodiments, at least one of the medical fluid therapy system 110 and the display system 120 may be connected to a network 130. According to some embodiments, the integrated system of the medical fluid therapy system 110 and the display system 120 may be connected to a network. In further embodiments, one or both of the medical fluid therapy system 110 and the display system 120 may be connected to a network. The network connection may be a hard wired or wireless connection to a network, for example, a local area network, or the Internet. According to some embodiments, the network may be a hospital network so the operation notes of the system 100 may be stored in the electronic medical record for the patient.

In some embodiments, all components or some of the components of the system 100 may be further connected directly (via wired connections) to another medical treatment therapy device, including, but not limited to, ECMO. In further embodiments, the readings may be transmitted via wireless network connection to other devices.

These components and operation of the system are described further below with respect to the figures.

Fluid Pump Housing

Figure 3:
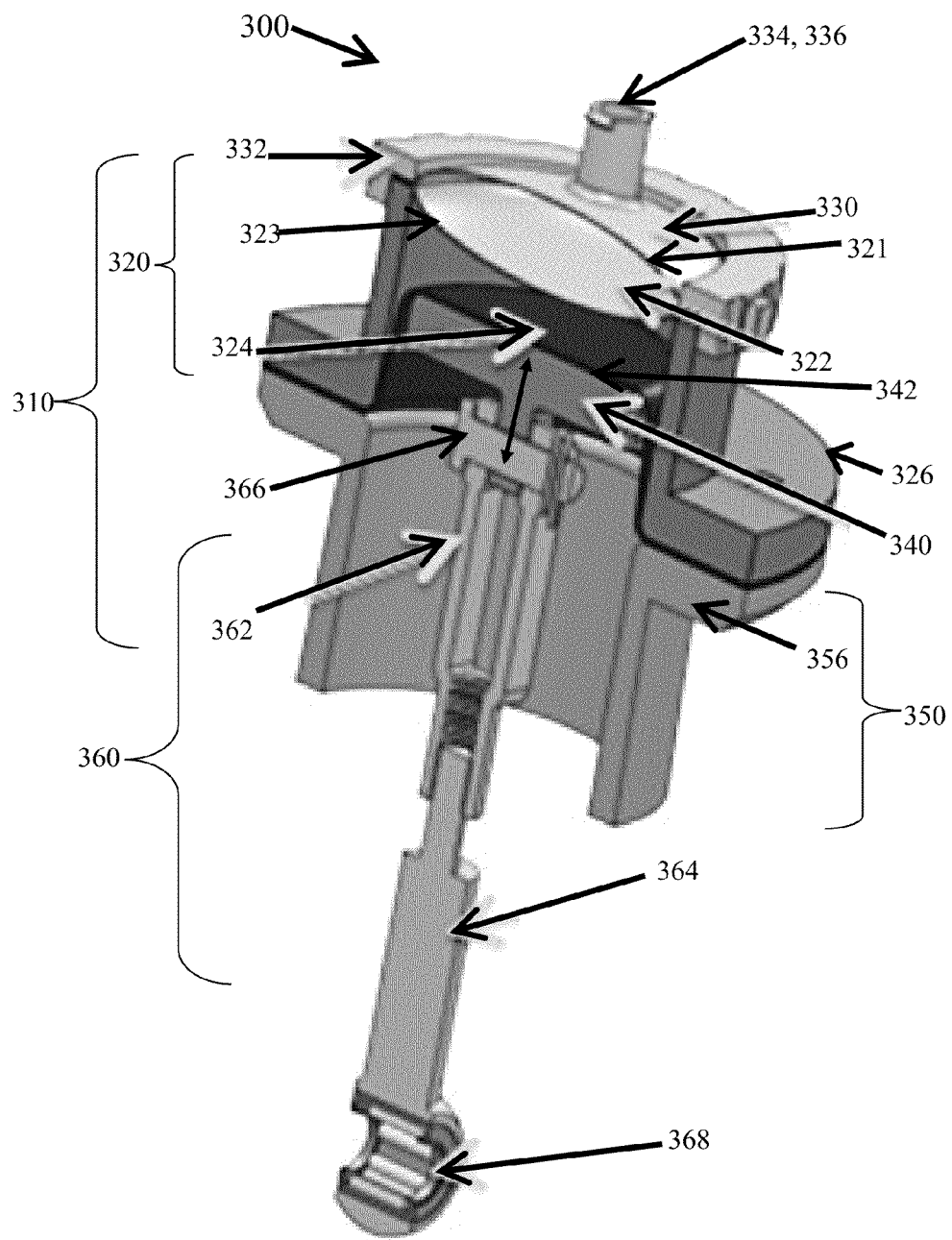
FIG. 3 is a sectional view of a fluid pump according to some embodiments.

FIG. 3 shows a sectional view of a fluid pump 300 according to some embodiments. According to some embodiments, the fluid pump 300 may include a housing 310. In some embodiments, the housing 310 may include at least one section. In some embodiments, the fluid pump 300 may include a first section 320 and a second section 350.

The first section 320 (may also be referred to as a fluid or blood compartment) may include a fluid chamber 322. The fluid chamber 322 may be a membrane configured to hold the fluid entering the pump. The chamber may be made of a flexible material, such as Gum Rubber. The chamber 322 may include at least two conduits: a first conduit (or inlet conduit) for fluid entering the pump and a second conduit (or outlet conduit) for fluid exiting the pump.

In some embodiments, the chamber 322 may be fixedly attached to and/or confined within the housing 310. The chamber 322 may include an upper surface 321 and a lower surface 323. The upper surface 321 of the chamber 322 may be bordered by a cap 330. The cap 330 may extend over a portion or the entire upper surface 321. In some embodiments, the cap 330 may be a rigid cap. In further embodiments, the cap 330 may be fixedly attached to the housing 310 by a fastener 332. In some embodiments, the fastener 332 may be a locking ring. In other embodiments, the fastener may be any known fastener.

In some embodiments, the cap 330 may include at least one connector or adapter for tubing. In some embodiments, the connector or adapter may be a port. In further embodiments, the cap 330 may include a connector or adaptor for each of the fluid conduits of the fluid chamber. In some embodiments, the cap 330 may include a first connector 334 and a second connector 336. In some embodiments, the connectors 334, 336 may be any known female luer lock posts.

The connectors may be positioned on the cap 330 as mirror images of each other. Each of the connectors may be in fluid connection with the respective fluid conduits of the fluid chamber 322. The connectors may overlap the respective fluid conduit so that the tubing is in fluid connection with the respective fluid conduit and may be configured to allow fluid to flow through the fluid chamber 322.

In some embodiments, the first section 320 may further include a cavity 324. The cavity 324 may be configured to fixedly hold an incompressible fluid or material. In some embodiments, the cavity 324 may be filled with saline. The cavity 324 may be below the chamber 322 and border the lower surface 323.

As shown in FIG. 3, the first section 320 may have a surface 326 that extends outwardly from the housing 310. The surface 326 may shaped like a flange. The second section 350 may have a surface 356 that extends outwardly from the housing 310. The surface 356 may also be shaped like a flange. The surfaces 326 and 356 may be of corresponding shape and size.

In some embodiments, the fluid pump housing 310 may further include a diaphragm 340. In some embodiments, the diaphragm 340 may be disposed between the first section 320 and the second section 350. In some embodiments, the diaphragm 340 may be fixedly attached to the housing between the first and second sections of the pump. The diaphragm 340 may be made of an elastomeric or flexible material, such as neoprene. Preferably, the diaphragm 340 is made of a material that is able to sustain a prolonged lifetime when repeatedly flexed. The diaphragm 340 may be a rolling diaphragm. The diaphragm 340 may have a flange design with a moldable o-ring that can be positioned between the first and second section. This configuration maintains proper orientation of a mechanical actuator 360 when attached to the diaphragm 340. The diaphragm 340 may include a surface 342 that may be configured to flex or move upon exertion of force by the mechanical actuator 360. In some embodiments, in resting (first) position, the diaphragm 340 has an ascending convolution into the section. The surface 342 extends in the second section substantially parallel to the cap 330.

In some embodiments, the diaphragm 340 may be configured to move from the resting position based on the movement of the mechanical actuator. The diaphragm 340 may be configured to move to second and third positions. In the second position, when the mechanical actuator 360 is moved away from the chamber 322, the surface 342 of the diaphragm 340 may be positioned further away from the cap 330 in the second section 350. In the third position, when the mechanical actuator 360 is moved toward the chamber 322, the surface 342 of the diaphragm 340 may be moved toward and into the first section and thus positioned closer to the cap 330. The surface 342 extends in the housing 310 substantially parallel to the cap 330 in the second and third positions.

The second section 350 of the fluid pump may include a mechanical actuator 360 configured to drive the diaphragm 340. In some embodiments, the mechanical actuator 360 may include a piston 362. In some embodiments, the piston 362 may be fixedly attached to the diaphragm 340 by a fastener. The fastener 366 is a cynoacrylate. In some embodiments, the fastener 366 may include a rolling bearing connected to a connecting pin of the rod. In further embodiments, the pump may include a rod 364. In some embodiments, the piston 362 may be connected to the rod 364 by a fastener, an adapter or connector 366. In some embodiments, the fastener 366 may include a connecting pin 365 and a roller bearing 367 (shown in FIG. 4).

All or some of the components of the pump housing may be sterilized and intended for single use.

According to some embodiments, the first and second sections and the cap may be made of materials such as Accura 60.

Fluid Pump Motor & Motor Housing

According to embodiments, the pump 300 may be actuated by a motor. The pump housing 310 may be removably attached to a motor by an adapter or connector. In some embodiments, the connector may be a rolling bearing. In some embodiments, the connector may be disposed at the end of the rod 364. For example, the rod may include a connector 368 shown in FIG. 3. The connector may be a roller bearing. In other embodiments, the connector may be placed on the piston.

In some embodiments, the motor mounts and connectors, such as roller bearings, may be made of stainless steel. The connecting pins, rods and pistons may be made of materials, such as Somos® NeXt.

In some embodiments, the fluid management systems may further include a motor. In some embodiments, the systems may include a motor for each pump included in the fluid management systems. In other embodiments, the systems may include a motor for two or more pumps.

In some embodiments, the pump may be actuated by a motor to move the fluid along the fluid path or loop. To move the fluid along, the fluid chamber may be deflected by transferring a force through the cavity that contains the incompressible solution from the diaphragm on the bottom that is driven by a piston. The motor may drive the mechanical actuator (piston and rod system). The driving of the actuator of the motor may also trigger the corresponding set of pinch valves allowing control of fluid direction.

The piston subsystem may be similar to that of a reciprocating piston in a combustion engine. A flywheel mounted to the motor may rotate providing periodic movement to a rod through a driving post and then on to a piston. The piston attached to a rolling diaphragm may transfer the force to an incompressible fluid (saline) which will then cause the deflection of the fluid chamber. The direction change from rotational to linear may be accommodated via a jointed coupling at the base of the piston attached to the rod. All motion may thereby be transferred to the membrane system.

In some embodiments, the motion of the mechanical actuator (the rod and piston system) may be a controlled by a controller and a motor. The motor may be a motor capable of being controlled by a main controller or a combination of controller system (such as an EtherNet/IP Drive) and motor.

In some embodiments, the pump may be disposed between a set of valves. The movement of the fluid chamber may be collectively controlled with respect with the valves and the motor. In particular, the deflection of the fluid chamber may provide a suction and expulsion of the fluid into and out of the fluid chamber, respectively, when synchronously paired to a set of pinch valves. When the valve prior to the pump is open and the valve after the pump is closed, the piston may be on the downstroke providing suction to pull the fluid into the chamber. Once the flywheel reaches bottom dead center (the piston moved as far away from the pump 300), the valves state changes and the piston causes the fluid to be expelled from the chamber. When the valve prior to the pump is closed and the valve after the pump is open, the piston may be on the upstroke providing force to move the fluid out of the chamber.

The configuration of the valves and pump allow for the reduction of fluid volume by not having to pass an internal compartment in an internal or pass-through type valve.

Figure 4:
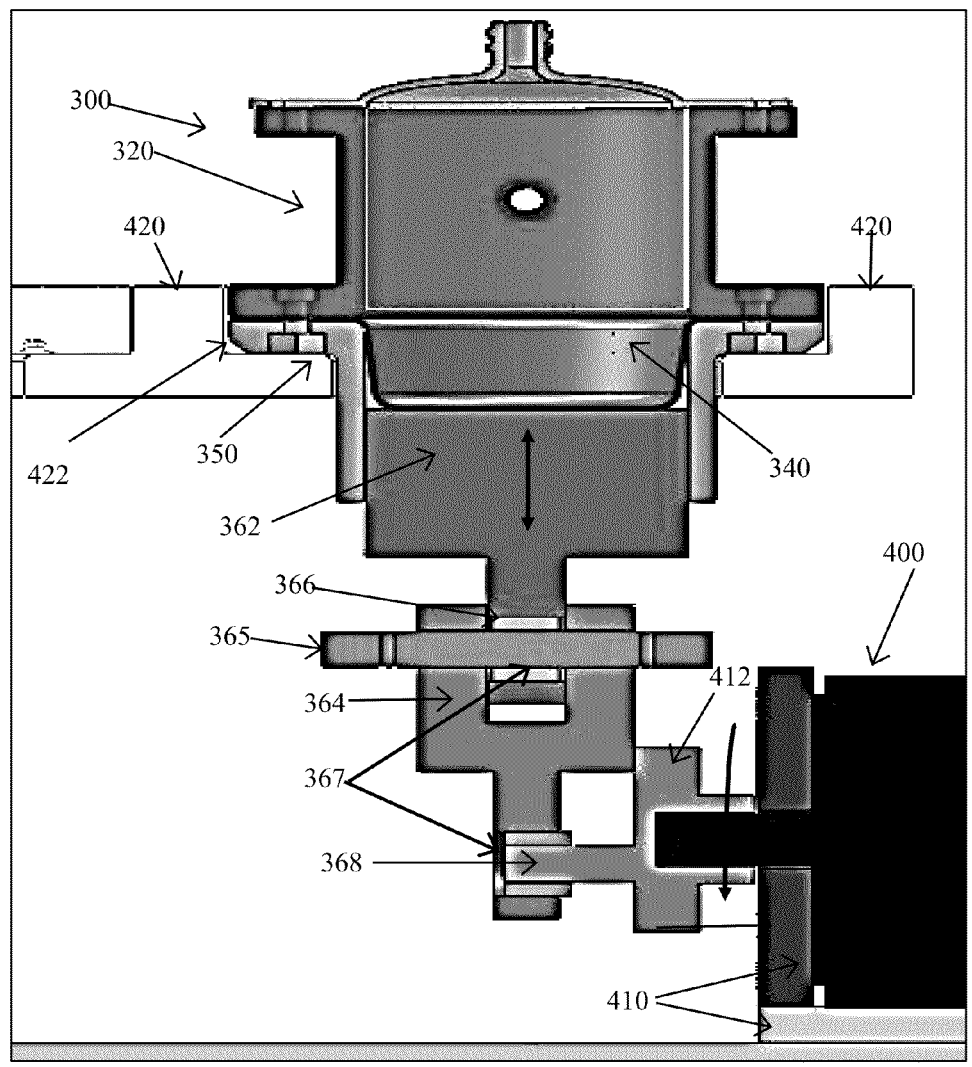
FIG. 4 is an enlarged view of a fluid pump within the system according to some embodiments.

FIG. 4 shows the pump 300 according to embodiments disposed within the system connected to a motor 400. As shown in FIG. 4, the motor 400 may further include a plurality of motor mounts 410. Although two motor mounts are shown in the figure, the system may include any number of mounts. The motor 400 may include a cam shaft 412 that is connected to the rod 364. The rod 364 may be connected via connector 368. The connector may be a roller bearing. The cam shaft may have a corresponding shape to the connector. The motor may have an encoder to allow for a closed loop feedback control system.

In some embodiments, the fluid management systems may further include a pump receiving member 420 for each pump of the system. According to some embodiments, the pump receiving member may be made of materials such as ACCURA® 60. Each pump receiving member may be structured and configured so that the pump has no remaining degrees of freedom to allow for a rigid system. The pump 300 may be disposed within the receiver. The pump receiving member may also be structured and configured to prohibit rotational motion. The receiver 420 may have a recess 422 that corresponds to the shapes of the extending surfaces of the first and second sections of the pump 300 (e.g., the flanges of the pump 300) so that the rotational motion is prohibited. The pump 300 may further be secured into position by fasteners, such as screws.

Fluid Circuits or Loops

According to some embodiments, the components of the devices and systems may be configured or designed to have a plurality of fluid treatment therapies. The fluid treatment therapies may be performed by fluid circuits or loops (paths). The devices and systems may include any number of fluid circuits or loops. The number of fluid circuits or loops of the devices and systems may be modified according to the fluid needs and functions needed for treatment of the patient. For example, the patient may not require the therapies provided by all of the fluid circuits or loops.

Figure 2:
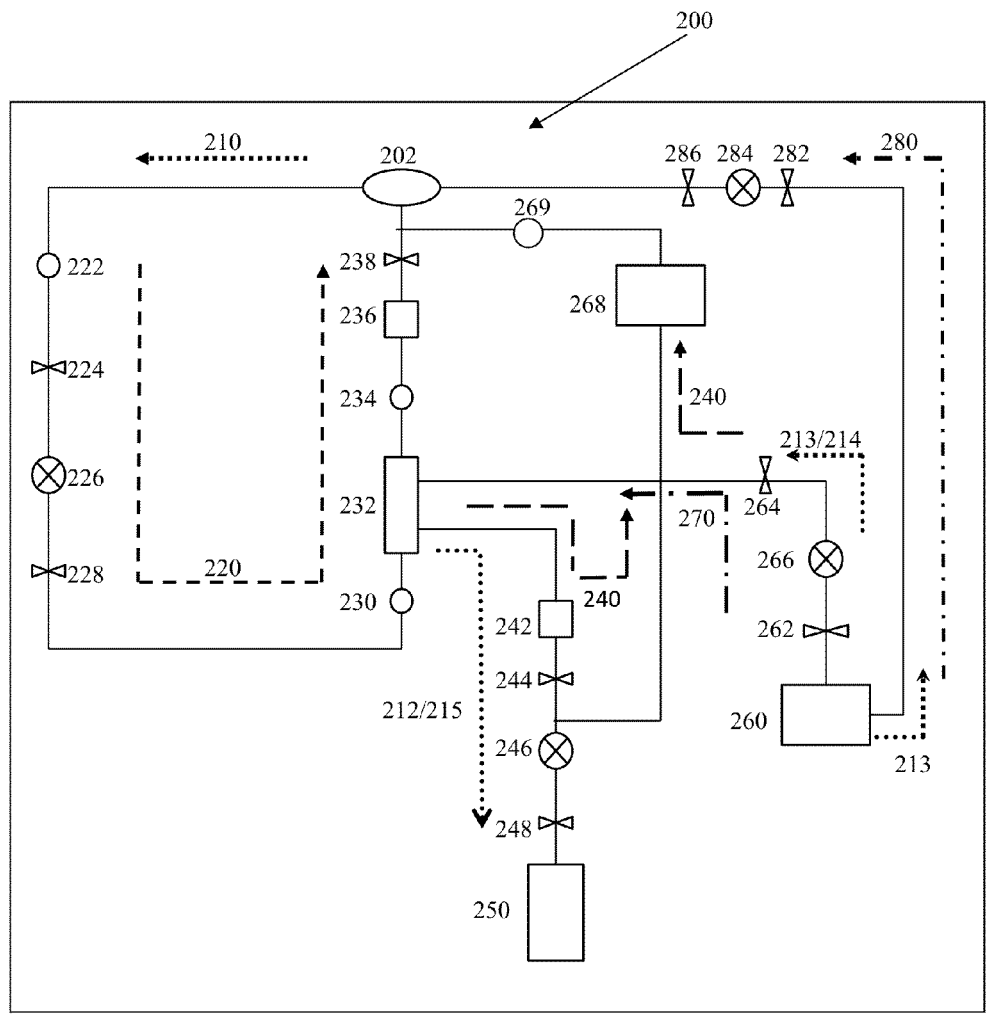
FIG. 2 is a schematic representation of the fluid systems of a medical fluid treatment system according to some embodiments.

In some embodiments, the devices and systems may be configured or designed to have any combination of the following fluid circuits or loops: a blood loop, a replacement fluid loop (CVVH mode), a dialysate loop (CVVDH mode), and an offset loop. FIG. 2 shows an example of a system 200 that includes a blood loop 220, a replacement fluid loop 240, a dialysate loop 270, and an offset loop 280.

The blood loop 220 may be a closed-loop path of blood 210 that is circulated out of a patient 202, filtered, replenished, and returned to the patient. The replacement fluid loop 240 may be the closed-loop path where the waste products from the blood are extracted and replaced with the substantially the same amount of a prescribed replacement fluid during the CVVH mode. The dialysate loop 270 may be the closed-loop path where dialysate is added to the hemofilter for extraction of the waste products from the blood during the CVVDH mode. The offset loop 280 may be the closed-loop path that is configured to allow an adjustment of the volume of replacement fluid by the clinician.

The blood loop 220 may include at least one fluid sensor 222 for sensing, detecting or measuring the flow characteristics or pressure, or combination thereof, of the blood 210 leaving the patient. In further embodiments, the blood loop 220 includes at least a first valve 224, a second valve 228, and a fluid pump 226. The first valve 224, the second valve 228, and the blood pump 226 may be collectively controlled (by a controller) to move the blood 210 through the fluid pump 226 like the embodiments described above.

In some embodiments, the fluid pump 226 may be configured to manage small volumes of blood. In some embodiments, the fluid pump 226 may correspond to the fluid pump 300 shown in FIG. 3 (described above). In other embodiments, the fluid pump 226 may correspond to other known fluid pumps.

The blood loop 220 may further include a hemofilter 232. The hemofilter 232 may be a semi-permeable membrane that provides a system by which toxins from the blood can be removed via a method of convective drag or dialytic clearance. The hemofilter 232 may include a plurality of ports. In some embodiments, the hemofilter 232 may include at least a blood input, a blood output port, a port for ultrafiltrate/dialysate output. In further embodiments, the hemofilter 232 may further include a dialysate input. The hemofilter 232 may be any known commercially available hemofilter. The blood loop may further include a sensor 230 before the hemofilter 232 and a sensor 234 after the hemofilter.

After the blood 110 exits the fluid pump 226 via valve 228, the blood flows through or by the sensor 230 before flowing through the hemofilter 232. The sensor 232 may be configured to detect or measure the fluid characteristics of the blood entering the hemofilter. The blood exiting the hemofilter may then flow through or by sensor 234 that measures the fluid characteristics of the blood exiting the hemofilter. The entering and exiting measurements may be compared by the system to determine the operation status of the hemofilter. If a malfunction or deterioration of the operation of the hemofilter is determined, the system may trigger an alarm (described further below).

In the CVVH therapy mode, as blood is pumped through the hemofilter, the toxins removed from the blood (as a result of the radial pressure) result in the creation of an ultrafiltrate through the pores in the membrane. The ultrafiltrate may then exit the hemofilter via the ultrafiltrate/dialysate output and flow to the ultrafiltrate collection reservoir or bag 250. In the CVVHD therapy mode, as blood is pumped through the hemofilter, dialysate enters the hemofilter via the dialysate input and is pumped through the hemofilter in the opposite direction of the blood flow on the opposite side of the membrane of the hemofilter. The pressures and dialysate remove the toxins from the blood and the toxins are thereby added to the dialysate through the pores in the membrane. The dialysate may then exit the hemofilter via the ultrafiltrate/dialysate output and flow through the dialysate fluid loop 170.

The systems may further include an air detector 236 and a third (emergency) valve 238. The air detector 236 and emergency valve 238 may be disposed in the blood loop directly before the blood returns to the patient. The air detector 236 may be any known air detector. The air detector 236 may use ultrasonic waves to determine whether there are any potentially hazardous air bubbles in the tubing before the blood returns to the patient. The tubing may be simply placed in the air detector and does not require any direct interaction with the blood. Upon sensing any significant amounts of air in the blood loop, the system may trigger and alarm and immediately prohibit any further flow by activating the emergency valve 238 until the loop has been purged of air. During the prime sequence, the air detector may also be disabled to allow for fluid to propagate the system. The prime sequence may be conducted without having a patient coupled to the system.

During the CVVH therapy mode, according to some embodiments, the systems may operate a replacement fluid loop 240. The ultrafiltrate 212 exiting the hemofilter 232 may enter the replacement fluid loop 240 toward the ultrafiltrate reservoir 250. The replacement fluid loop 240 may include a blood detector 242. The blood detector 242 may be any known blood detector. The blood detector 242 may be placed in the replacement fluid loop 240 after the hemofilter 232. The tubing may be run through the detector 242 without interacting with the ultrafiltrate. The blood detector 242 may be configured to detect the operation status of the hemofilter 232. For example the blood detector 242 may be configured to detect color changes in the ultrafiltrate exiting the hemofilter 232. Based on the detection, the system may be configured to trigger an alarm alerting personnel that there may be a hemofilter operation error, such as rupture in the hemofilter that would indicate a need to change hemofilters.

The replacement fluid loop 240 may include a fluid balance system. The fluid balance system may be configured so that the volume of replacement fluid is added from the replacement fluid reservoir 260 is the same as or substantially the same volume of ultrafiltrate removed from the blood. In some embodiments, the fluid balance system may include two fluid pumps that are individually controlled to be offset of each other. The pumps may be controlled so that the motions are directly opposite of each other. By setting the two pistons motion directly opposite of each other, (substantially or near) perfect fluid balance may be achieved. The first pump may receive the ultrafiltrate that exited the hemofilter and the second pump may receive the replacement fluid that will replace the ultrafiltrate removed from the blood. As shown in FIG. 2, the replacement fluid loop 240 may include pump 246 for pumping the ultrafiltrate to the ultrafiltrate (collection) reservoir 250 and pump 266 for pumping the replacement fluid from a replacement fluid reservoir 260.

The system may further include a set of valves for each of the pumps. As shown in FIG. 2, the pump 246 may be between (fourth) valve 244 and a (fifth) valve 248. The pump 246 may be configured to pump the ultrafiltrate 212 removed via the hemofilter 232 to the ultrafiltrate collection reservoir 250. The pump 266 may be between (sixth) valve 262 and (seventh) valve 264. The pump 266 may be configured to pump the same or the substantially the same volume of replacement fluid 213 from the replacement fluid reservoir 260 as the volume of ultrafiltrate 212 collected in the ultrafiltrate collection reservoir 250. Each set of valves and the pump may be collectively controlled (by a controller) to move the blood through the respective fluid pump like the embodiments described above.

In some embodiments, the fluid balance system may include two motors that each controls one of the two pumps. In other embodiments, the fluid balance system may include one motor that separately controls the two pumps. In these embodiments, a controller may individually control the collective configuration of set of valves and pump for the replacement fluid and the collection configuration of set of valves and pump for the ultrafiltrate. In some embodiments, the fluid balance system may include the same or different pumps.

Figure 5:
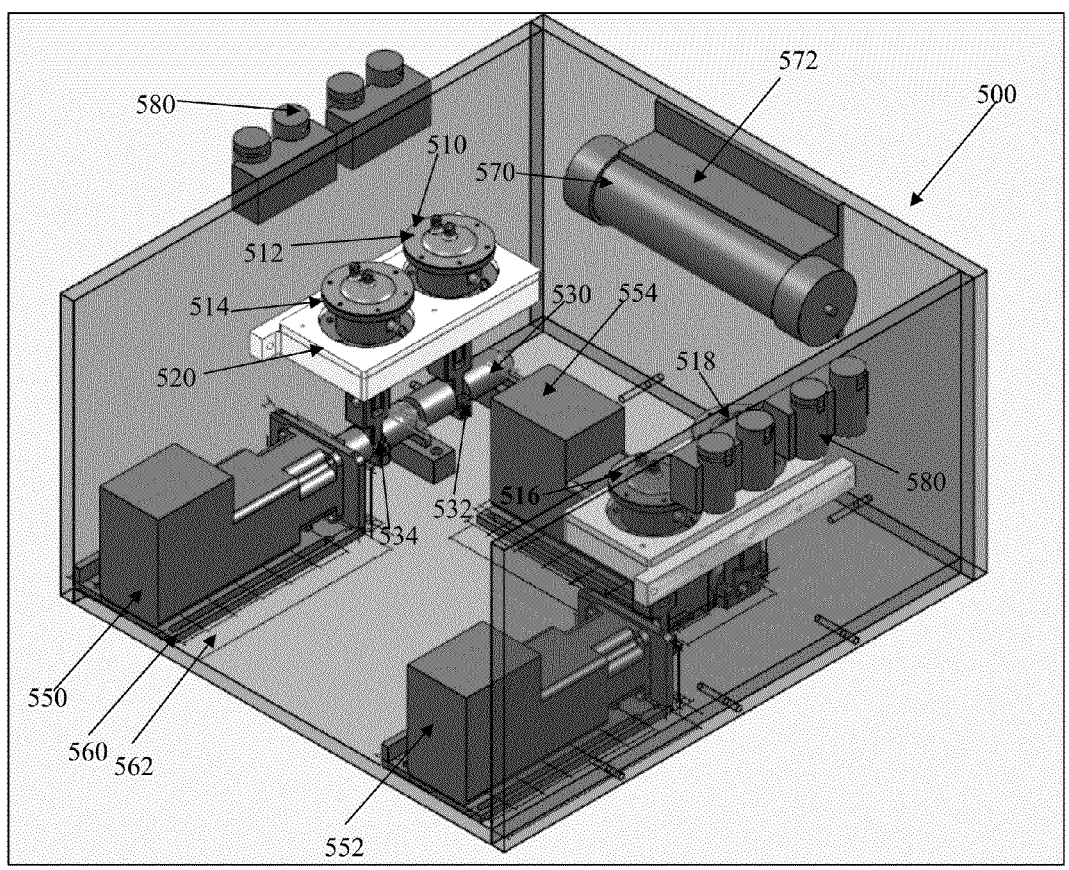
FIG. 5 is a view of a medical fluid treatment system according to some embodiments.

In some embodiments, both or one of the pump housings of the fluid balance system may correspond to the pump housing shown in FIG. 3. FIG. 5 shows an example of a system 500 having a fluid balance system 510 that includes two pump housings like the housing shown in FIG. 3. As shown in FIG. 5, the fluid balance system 510 may include two pumps 512 and 514. These pumps 512 and 514 may be respectively connected to pistons 532 and 534. The pistons of these pumps may be linearly offset. For example, one of the pistons 532 and 534 may have a starting position in the uptake position and the other one of the pistons 532 and 534 may have a starting position in the opposite position, the downtake position.

FIG. 5 shows the two pumps 512 and 514 connected to a single shaft 530 connected to a single motor 550. The motor may be capable if and configured to drive the two pumps simultaneously, thereby a single drive system powers two mechanically coupled pumps.

According to some embodiments, the shaft 530 may include a first gear that interfaces and meshes with a second gear. The second gear may be configured to serve two purposes—the first is to transfer the rotational motion of the motor to the pump system described in the blood loop, the second is to concurrently transfer rotational motion to a shaft by which another flywheel is connected on the opposing end. The shaft may be supported via two roller bearing stands mounted to the enclosure. By having the second gear and flywheel mounted in such a fashion on a common shaft whereby the driving posts are 180° out of phase respective to each other, a perfect or near perfect fluid balance may be achieved. When the flywheel controlling the ultrafiltrate is on an upstroke, the flywheel controlling the replacement fluid will be in the exact same position on a downstroke.

These embodiments also address the common issue associated with the production of ultrafiltrate through a hemofilter—the rate of production of ultrafiltrate. Due to the nature and efficiency of hemofilters, the initial ultrafiltrate production rate at the beginning of a cycle may be quite brisk and be higher than desired. To counteract this phenomenon, the coupled pump system according to may provide fluid balance by allowing the system to run as intended. In other embodiments, the valves may be actuated to further counteract this phenomenon. The valves may be actuated via the control system to reduce the flow to a prescribed amount. The back-pressure of the system will prevent the flow from continuing down the path. Positive pressure will not be created by nature of obstructed tubing path providing a controlled closed system. By using the same pump system as the blood pump, costs may also be reduced and uniformity among subsystems may be allowed.

Figure 6:
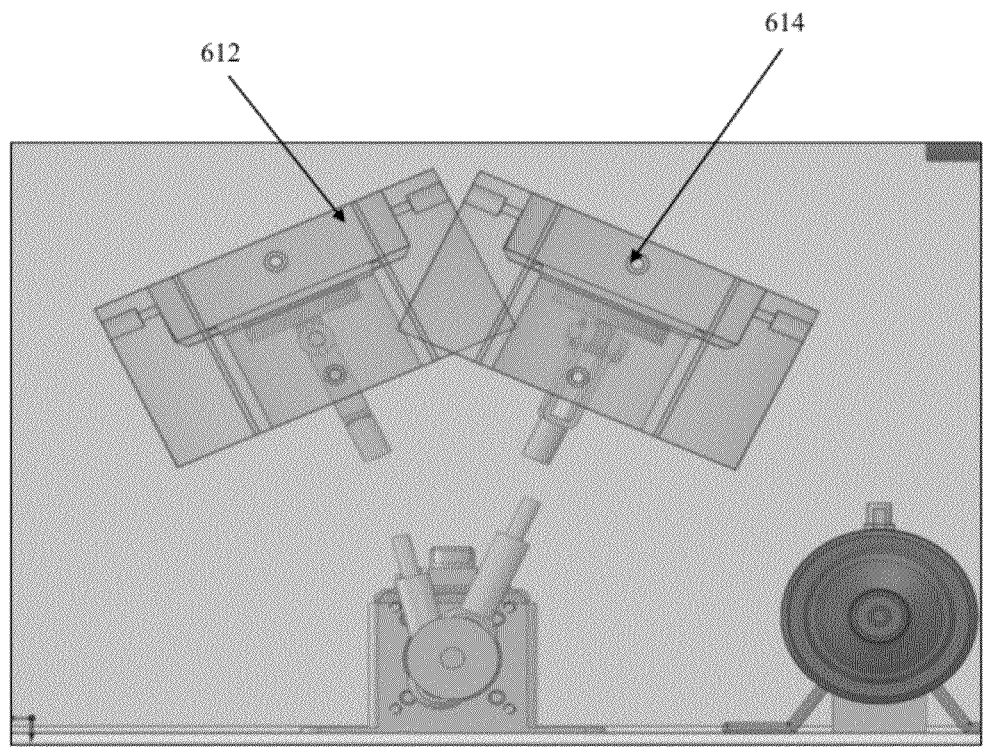
FIG. 6 is a view of a medical fluid treatment system according to other embodiments.

In other embodiments, two pumps 612 and 614 may be attached to pistons in a V-type configuration of the pump systems with a single motor providing the driving force through a crankshaft to two pistons as shown in FIG. 6. The pump housing may be same as or similar to the pump housing shown in FIG. 3.

In other embodiments, the fluid balance system may be any known fluid balance system, such as the system described in U.S. application Ser. No. 12/663,253, which is incorporated in its entirety.

In some embodiments, the replacement fluid loop 240 may include a fluid heater 268. The fluid theater 268 may be any known fluid heater. The fluid heater 268 may address the thermal concerns in the blood loop and replacement fluid loop. Because of convective heat transfer between the blood, tubing, and ambient air temperatures, a fluid heater may be placed after the hemofilter 232 and before the patient 202. The heater 268 may be configured to heat replacement fluid 213 that will be mixed with blood 210 directly before return to the patient 202. The heater 268 may also be configured to maintain the standard core temperature with both upper and lower limits to prevent hypothermia or hyperthermia in the patient.

The replacement fluid loop 240 may further include at least one temperature monitor detector or system 269. The temperature monitoring system 269 may be combined or separate from the fluid heater 268. The temperature monitoring system may include at least one of known temperature sensor. The temperature monitoring system may be disposed at one or a plurality of locations along the replacement fluid loop to provide a closed loop feedback system to allow for the device to adjust fluid temperature and process temperature data in real time. The heater may be isolated from the loop for the benefit of sterility. The replacement fluid 213 may be heated convectively when passing through a heated area while still contained in its tubing.

During the CVVHD therapy mode, according to some embodiments, the systems may operate a dialysate fluid loop 270. During this mode, the dialysate or replacement fluid 213 may be pumped from the replacement fluid or dialysate reservoir 260 via the pump 266 and valves 262 and 264 configuration. Although the figures show that the dialysate 214 is pumped from the same reservoir from which the replacement fluid is pumped for the fluid balance loop, the system, in other embodiments, may include a separate reservoir for the dialysate. The controller controls the flow rate and volume of the dialysate removed from the reservoir via the pump configuration. The dialysate 214 is then pumped to the hemofilter 232. The dialysate 214 enters the hemofilter via a dialysate port. The hemofilter 232 then removes the toxins and disposes of the discarded dialysate 215. In some embodiments, the hemofilter disposes of the discarded dialysate through the same flow path as discarded ultrafiltrate. For example, the discarded dialysate 215 flows through the blood detector 242, the pump 246 via the operation of valves 244 and 248, to the ultrafiltrate/dialysate reservoir 250 for collection.

According to some embodiments, the systems may also include an offset loop 280. The offset loop may provide adjustability for any deviations from the replacement fluid loop. For example, in certain conditions, clinicians may need to impose a positive or negative state of fluid balance. The offset loop will provide this functionality.

In some embodiments, the offset loop 280 may include valves and pump configuration similar to the blood loop. The offset loop 280 may include a (eighth) valve 282 and a (ninth) valve 286 and pump 284. The pump 284 may be the same as or similar to pump shown in the figures. The pump 284 and valves may be collectively controlled to control the volume of replacement fluid via the replacement fluid reservoir 260 to be added or removed from the replacement fluid 213 to be provided to the patient 202.

Configuration of Devices and Systems

In some embodiments, the system may be housed in a modular or portable unit. The modular unit may have housing configured to control sterility of the system. For example the components of the system may be disposed at different self-contained sections of the housing. The self-contained sections may improve sterility of the system. The sections may be separated by an overlay or surface. The surface may be made of a plastic or acrylic material.

In some embodiments, the housing may include a plurality of sections. In some embodiments, the mechanical components and electronics of the system may be self contained and separated from the (single-use or replaceable) items connected to the system via connectors and/or adapters. For example, the processing components such as controllers may be provided underneath the mechanical components (such as the motor) in a self-contained section. The mechanical components may be further separated from the single-use items (such as the pump and tubing) in a self-contained section. These items may include but are not limited to the pump housing that may be connected to the motor within the housing as well as tubing that connects to the replacement fluid reservoirs and ultrafiltrate (collection) reservoirs. According to some embodiments, the replacement fluid reservoirs and ultrafiltrate (collection) reservoirs may be external to the system housing and connected to the system via medical tubing.

FIG. 5 shows an example of the modular housing (with the tubing not shown).

In some embodiments, the housing may include adapters or connectors configured for the connectable system components. The connectors may be configured to removably attach the connectable system components to the housing or system so that the connectable system components can be connected to the system during operation and may then later be removed and replaced with new components. In some embodiments, the components of the system may include connectors or adapters configured to receive the connectable system components. For example, pinch valves 580 may each include a connector for the tubing extending from the pumps. The hemofilter 570 may also include a connector or receiver 572 to receive a hemofilter.

In some embodiments, the system 500 may include at least one pump receiving member 520. The pump receiving members 520 may be configured to have a depression in a surface to receive each pump. FIG. 5 shows four pump receiving members, one pump receiving member for each pump. The pump receiving members 520 may be configured to receive any pump of the system, for example, pumps 512, 514, 516, and 518. The pumps may be for the replacement fluid loop, as well as the pumps for the other loops of the system. The pump receiving member 520 may be made of an acrylic material that is capable of being sterilized. Although only a portion is shown, it would be understood that each pump receiving member 520 may be a part of a housing divider configured to separate and self-contain the mechanical components, such as motors 550 and 552 from the connectable system components.

It will be further understood that the processing components, such as controller 560 may be further separated from the mechanical components by a self-containing layer 562.

According to some embodiments, a motor may drive to at least one pump. As shown in FIG. 5, the motor 550 may be connected to and drive the fluid balance system including pumps 512 and 514. The other pumps, 516 and 518, configured for the blood and offset loops, may each be connected to and be configured to be driven by motors 552 and 554, respectively.

Connectable/Disposable System Components:

According to some embodiments, the system may be configured to receive single use or disposable connectable items. In some embodiments, these items may be sterilized.

According to some embodiments, the items may include but are not limited to the pump housing, tubing, and hemofilter. According to some embodiments, a portion or combination of the single use items may be sold as kit.

In some embodiments, the kit may include at least one pump housing that includes all or portions of the pump housing shown in FIG. 3. The pump housing will at least include a connector, such as roller bearing, configured to connect to a motor of the system. In further embodiments, the kit may include a plurality of pump housings. For example, in some embodiments, the kit may include one, two, three or four pump housings. In alternative embodiments, the kit may include additional pump housings.

In further embodiments, the kit may include tubing for the system. The tubing may be in addition to or in alternative to the pump housing. In some embodiments, the kit may further or alternatively include a tube frame. The tube frame including sections for disposing all or most of the tubing. The tubing may be configured as a part of the tube frame.

In further embodiments, the kit may include at least one connector configured to connect the tubing and/or pump to the system.

In further embodiments, the kit may include a hemofilter. The hemofilter may be in addition to or in alternative to the pump housing and tubing.

Control Module and Display

According to some embodiments, the display system may further include a user interface. In some embodiments, the instructions for user interface may be programmed and stored in the memory of the display system. In other embodiments, the instructions for the user interface may be programmed and stored in the memory of the fluid therapy system. In further embodiments, the instructions for the user interface may be programmed and stored remotely and accessed by either or both the display system and the fluid therapy system.

According some embodiments, the user interface may be programmed to control or provide instructions to control the systems and devices of the disclosure. The user interface may control or provide instructions to control the systems and devices of the disclosure based on inputs entered by the user into the user interface using an input device. According to embodiments, the controller(s) may control the system according to the inputs.

According to the some embodiments, the inputs may include treatment mode. Treatment modes may include but are not limited to CRRT, CVVH, CVVHD, and CVVHDF modes. One or a combination of the treatment modes may be selected. In other embodiments, the inputs may further include another or adjunct medical fluid treatment therapy or extracorporeal treatment systems and devices (also referred to as other medical fluid treatment therapy systems and devices) for which the system will be used in conjunction. In some embodiments, the system may be connected to the other medical fluid treatment therapy systems and devices. In further embodiments, the controller may control the other medical fluid treatment therapy systems and devices. These other devices may include but are not limited to an ECMO device, cardiopulmonary bypass device, ventricular assist device, plasma exchange device, apheresis device, or hemoperfusion device. According to further embodiments, the inputs may further include patient type, such as pediatric or adult.

The inputs may further include operating parameters. In some embodiments, the operating parameters may be specific to the mode, adjunct therapy, other connected devices, patient type, or any combination thereof. In some embodiments, any or all of the operating parameters may be stored for each mode, adjunct therapy, other connected devices, patient type, or any combination thereof. In further embodiments, the controller may automatically control all or any of the operating parameters for the system based on the mode, adjunct therapy, other connected devices, patient type, or any combination thereof selected. In other embodiments, the user may input all or any of the operating parameters for the mode, adjunct therapy, other connected devices, patient type, or any combination thereof selected.

Figure 8:
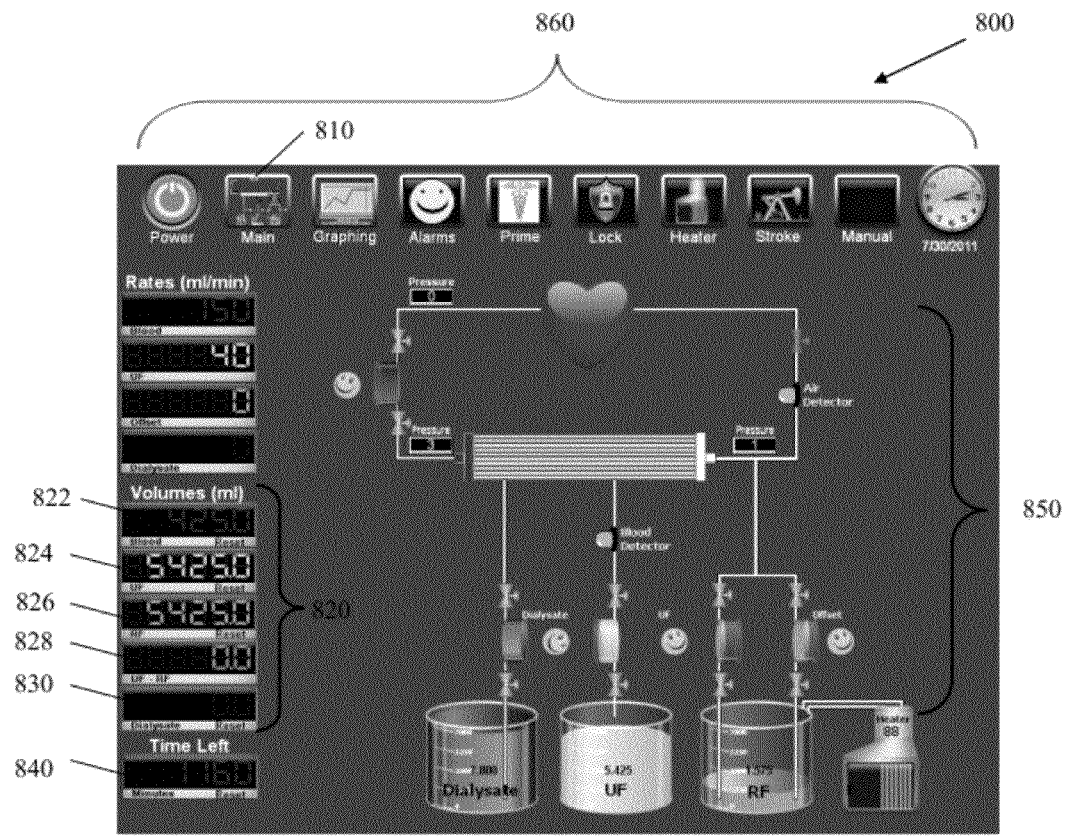
FIG. 8 is a main screen view of the user interface according to some embodiments.

According to some embodiments, the operating parameters may be inputted or entered into the user interface using an input device such as a keyboard or a touch screen. In some embodiments, the operating parameters may be entered on the main screen shown in FIG. 8, which may be accessed via button 810. In some embodiments, the inputted operating parameters may be adjusted during operation, for example, by selecting the reset button.

According to some embodiments, the operating parameters may be entered by selecting an operating parameter shown on the screen. In some embodiments, the operating parameters may include volumetric flow rates 820 for several parameters. The flow rates may be set for any one or combination of operating parameters. The operating parameters may, include, but are not limited to, blood 822, ultrafiltrate (UF) 824, replacement fluid (RF) 826, offset (UF-RF) 828, and dialysate 830. In some embodiments, the volumetric flow rates may be inputted in mL/min. In further embodiments, the ranges for inputted flow rates may be predetermined. Thee ranges may be based on the patient type, such as an adult or a pediatric. For example, the blood volumetric flow rate may be limited to the range of 0 to 150. The UF, dialysate, and offset volumetric flow rates may also be limited to a predetermined range. In further embodiments, users may be able to input a flow time in hours or minutes in time left field 840. The remaining flow time may also be displayed in that or a different field. The countdown may be helpful indicator when the materials, such as the replacement fluid or dialysate, may be getting low.

Figure 15:
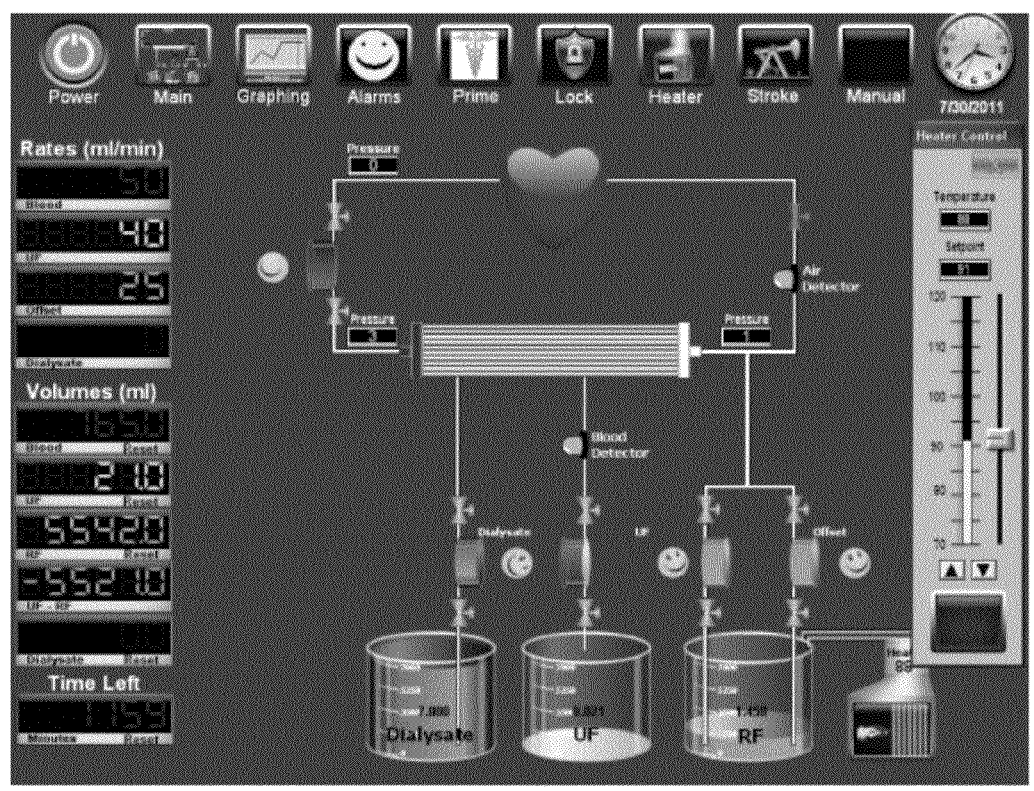
FIG. 15 is an example of a heater screen of the user interface according to some embodiments.

The user may start delivering therapy via the systems according to the embodiments by selecting the power button. Once the system is power, the graphical representation 850 of the operation status of the system may be visible on the display screen. The operating status may include but are not limited to the status of the pumps in motion, valves opening and closing, fluid volumes, status of blood and air detectors, patient exit pressure, filter enter pressure, patient enter pressure, heater temperature, and time remaining For example, the screen shown in FIG. 15 shows an input screen for adjusting the heater temperature. While the device is running, flow rates may be adjusted and counters may be reset.

The user interface may include certain operation protocols when certain conditions, such as air or blood are detected. For example, operation protocols may include automatically shutting down the machine and setting an alarm condition. The alarm condition may be programmed so that the condition must be cleared before the system will restart. The operating protocols may be manually bypass or modified based on the needs of the user. In some embodiments, the operation protocols may not be adjusted unless the user has higher level access, such as administrator access to the user interface.

The user interface may further include at least one accessory screen. The screens may include but are not limited to graphing, alarms, prime, lock, heater, stroke, and manual. These screens may be accessible by fields or icons on 860 the top of each screen.

Figure 7:
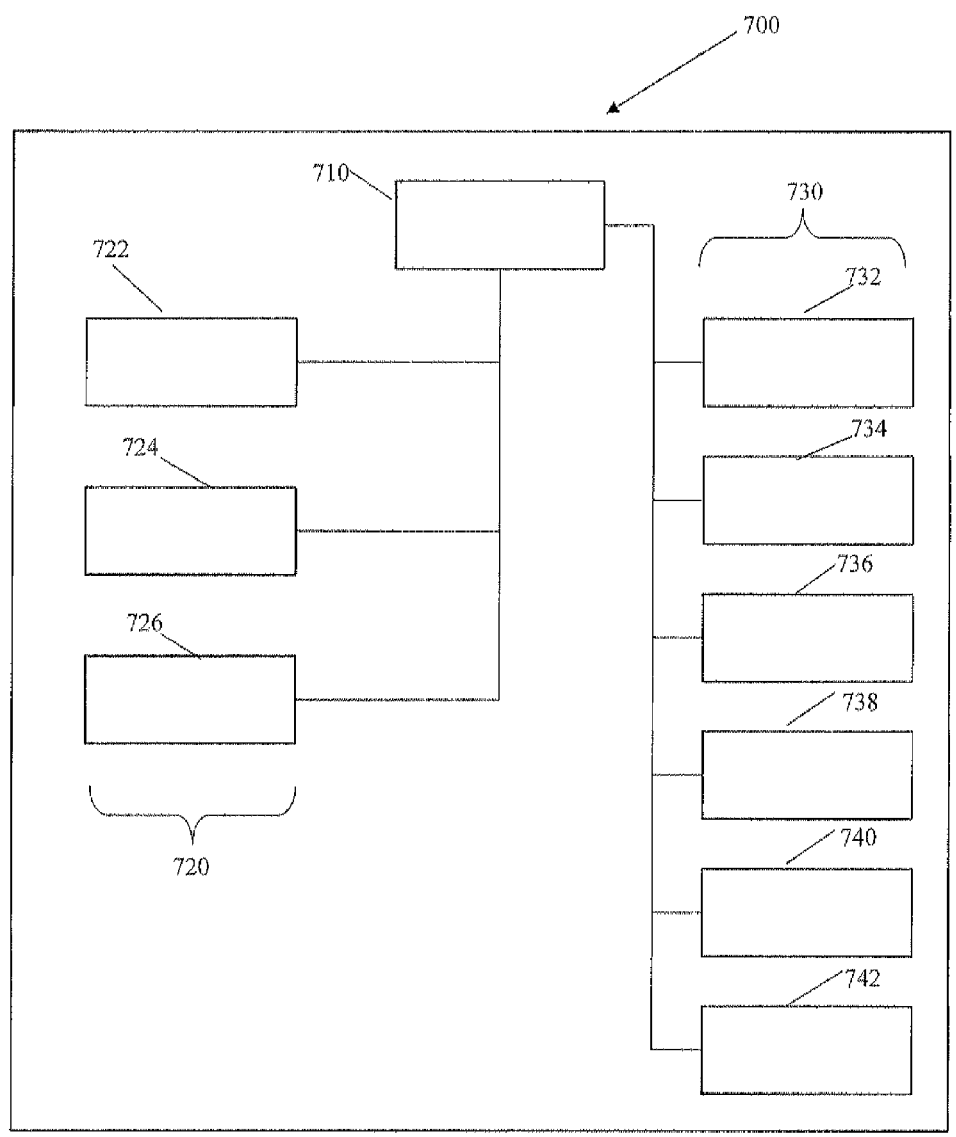
FIG. 7 is a schematic representation of a controller of the system according to some embodiments.

According to some embodiments, the controller may control the system based on the operating parameters. The controller may also control the system based on the operation status of the system. FIG. 7 shows the schematic 700 of the control parameters for a controller 710. In some embodiments, the controller may control the system by transmitted outputs 730 to the system. In further embodiments, the controller may control a connected or adjunct therapy device(s) by transmitting outputs 730 to the connected or adjunct therapy device(s).

In some embodiments, the outputs may be based on inputs 720 received regarding the operating status of the system. The outputs may be based on the comparison of the received inputs to the prestored or inputted operating parameters.

The inputs 720 may be based on the sensors and/or detectors included in the system. The sensors and/or detectors may include but are not limited to fluid sensor(s) 722, detector(s) 724, and temperature sensor(s) 726. In other embodiments, the inputs may be received from other and additional sensors and detectors from the system. In other embodiments, the inputs may be received from other systems, such as connected or adjunct therapy devices.

The controller may receive information from the fluid sensors 722. The information may include but is not limited to the fluid characteristics of the fluid(s) flowing through the system, such as blood, replacement fluid, ultrafiltrate, and dialysate. In some embodiments, the detectors 724 may include but are not limited to the blood detector and air detector. The information may receive information from the detectors 724. The information may include but is not limited to the detection of air in the blood or blood in the ultrafiltrate. In some embodiments, the temperature sensors 726 may provide information regarding the fluid flowing through the system.

According to the inputs, the controller may transmit one or more outputs to the system. In other embodiments, the controller may transmit one or more outputs to another system. In some embodiments, the outputs may be transmitted to hardware elements of the system. The hardware elements include but are not limited to memory 732, pinch valve(s) 734, display 736, replacement fluid heater 738, pump(s) 740, and protocols 742.

According to some embodiments, the controller may transmit the information received from the inputs to a memory device for storage. In further embodiments, the information received from the inputs may be transmitted to a network computer for storage. The controller may also transmit a record of any or all of the transmitted outputs, such as the control instructions), to a memory or network computer for storage. The controller may also transmit the information received from the inputs to a display device for display. In further embodiments, the controller may transmit record of any or all of the transmitted outputs to a display device for display.

The controller may also control the system based on the inputs. In some embodiments, the controller may control any one or combination of the pinch valve and pump systems based on the inputs. The controller may control the operation status of the pinch valve and pump system. The operation status may include but is not limited to timing, dwell angle, the flow rate, and offset. In further embodiments, the controller may control replacement fluid heater 738. The controller may cause the heater to increase or decrease the heat produced. In further embodiments, the controller may control the system according to protocols when the controller receives inputs of certain conditions. The protocols may include but are not limited to automatically shutting down the system, shutting down a component of the system, or activation of an alarm.

According to some embodiments, the controller may also transmit the information received from the inputs and/or the record of the outputs to connected or adjunct therapy devices.

Figure 9:
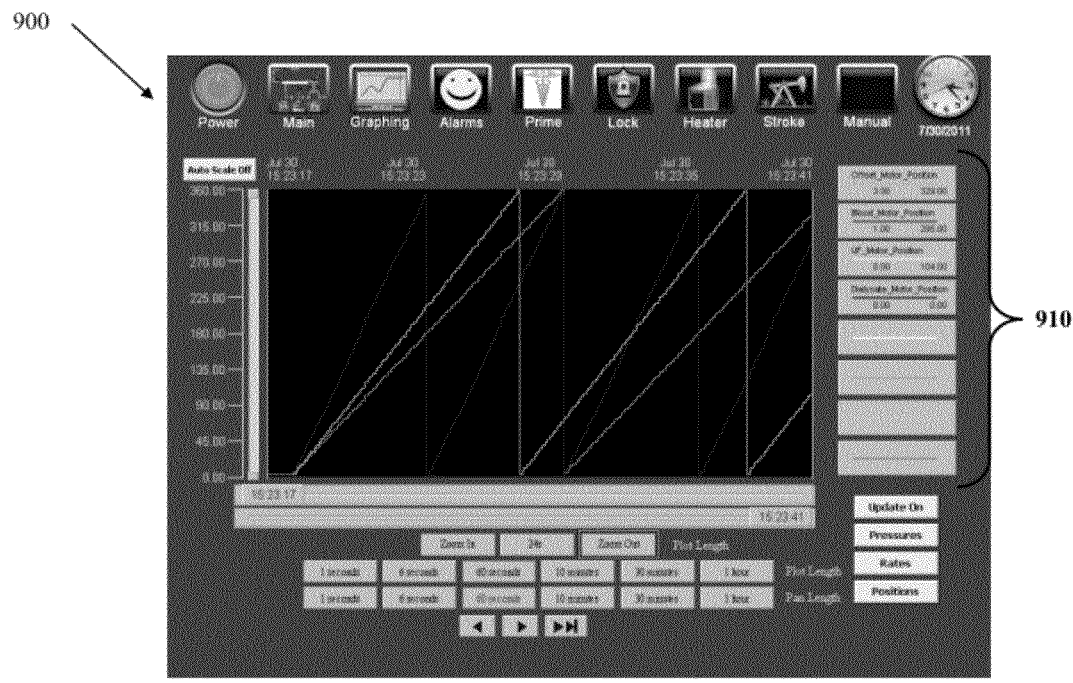
FIG. 9 is a graphing screen view of the user interface according to some embodiments.

According to some embodiments, the accessory screens may include a graphing screen, like the screen 900 shown in FIG. 9. The graphing screen may allow the user to view the operating parameters of the system based on date/time group process variables. These variables may include but are not limited to volumetric flow rates, motor speed, and blood pressures. The user interface may be programmed to process these variables to a SQL server database that could then be queried by any medical record system. Parameters of interest could either be sampled at some pre determined interval, such as an hourly or daily interval, or be event driven like a process variable exceeding the alarm limit.

The display system may be connected to the local area network via Ethernet making remote viewing possible. This would enable others to see the process variables using the graphing screen without having to physically be in the patient's room. Someone else could, from a distance, trouble shoot a faulty detector and recommend corrective action.

The graphical trend shown in FIG. 9 may have any number of parameters for simultaneous observation. The screen shows eight possible parameters 910 but may be include additional parameters. The parameters may be programmed or selected to update every few seconds or zoom in and out at an area of interest. This will provide t the ability to perform real time data acquisition. Also, this screen may be valuable and helpful when troubleshooting the system, such as a faulty transducer or when correlating the effect of a pump speed change on filter differential pressure.

Figure 10:
FIG. 10 is an alarm screen view of the user interface according to some embodiments.

The accessory screens may further include an alarm history screen and an alarm summary screen. The alarms may be activated when the controller determines based on the sensor or detectors that at least one component of the system is not operating properly. The alarm history screen, an example shown in FIG. 10, may provide access to all alarms that have ever occurred. The alarm summary screen may be configured to display active alarms which have not been acknowledged. When there is an active, the user may be notified. For example, the smiley face icon, as shown in the main screen 800, in the Alarms button, may change into a flashing red mad face to indicate there is a problem. Acknowledging a critical alarm that has shut down the unit may allow the system to be restarted; however, unless the fault is corrected it will just shut down again. Faults may be predefined or defined according to the lower and upper limits of the process variables being exceeded.

Figure 11:
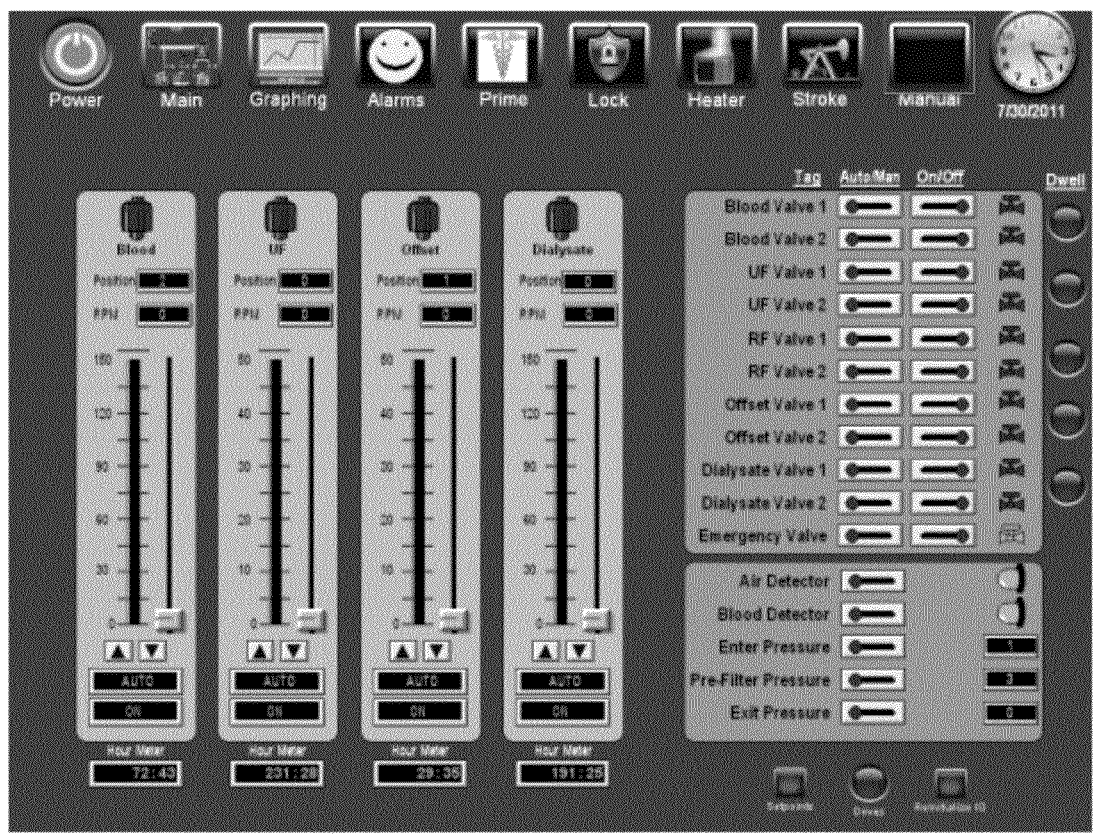
FIG. 11 is an example of a manual screen of the user interface according to some embodiments.

The accessory screens may further include a manual screen, as shown in FIG. 11. The manual screen may allow access for manual operation and configuration of the system. This screen may be password or credential protected for a higher administrator, repair, maintenance, or biomedical engineering use. From this screen, the user may manually override the operation of the system. For example, a user may manually disable the air and blood detector, bypass the pressure transmitters, and change the dwell angle on the valve opening and closing for example. The user may be able to enter set points for pump volumes and alarm pressures.

Figure 12:
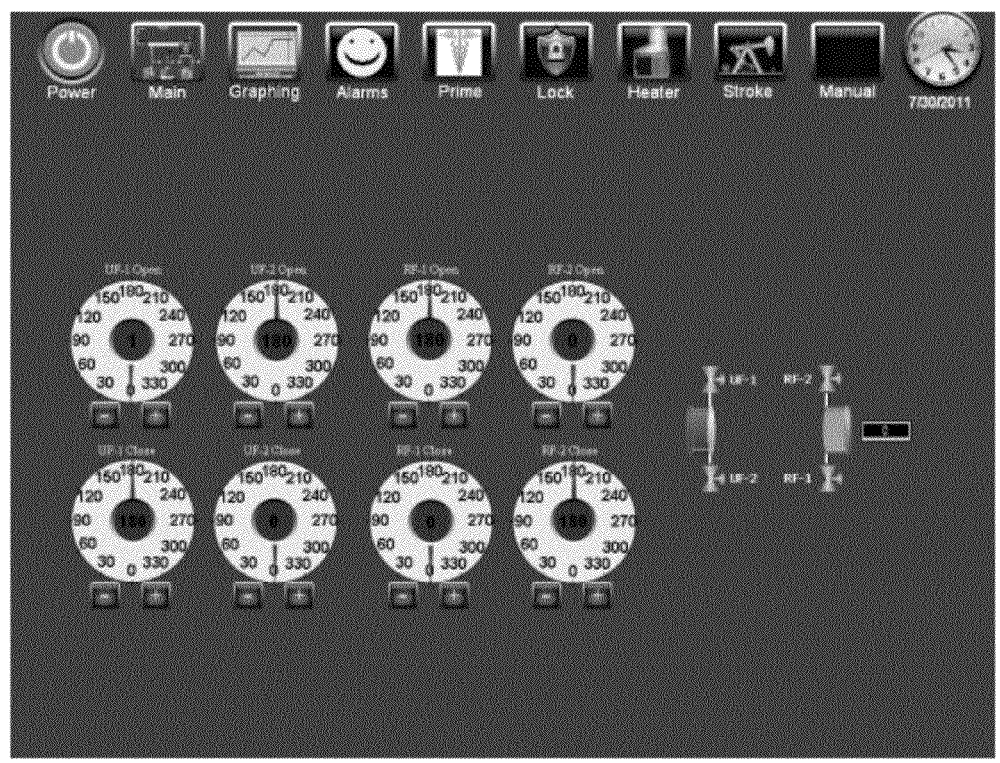
FIG. 12 is an example of a valve dwelve screen of the user interface according to some embodiments.

The accessory screens may further include a valve dwell screen as shown in FIG. 12. The valve dwell screen may display the dwell angle of each valve in operation in the system.

Figure 13:
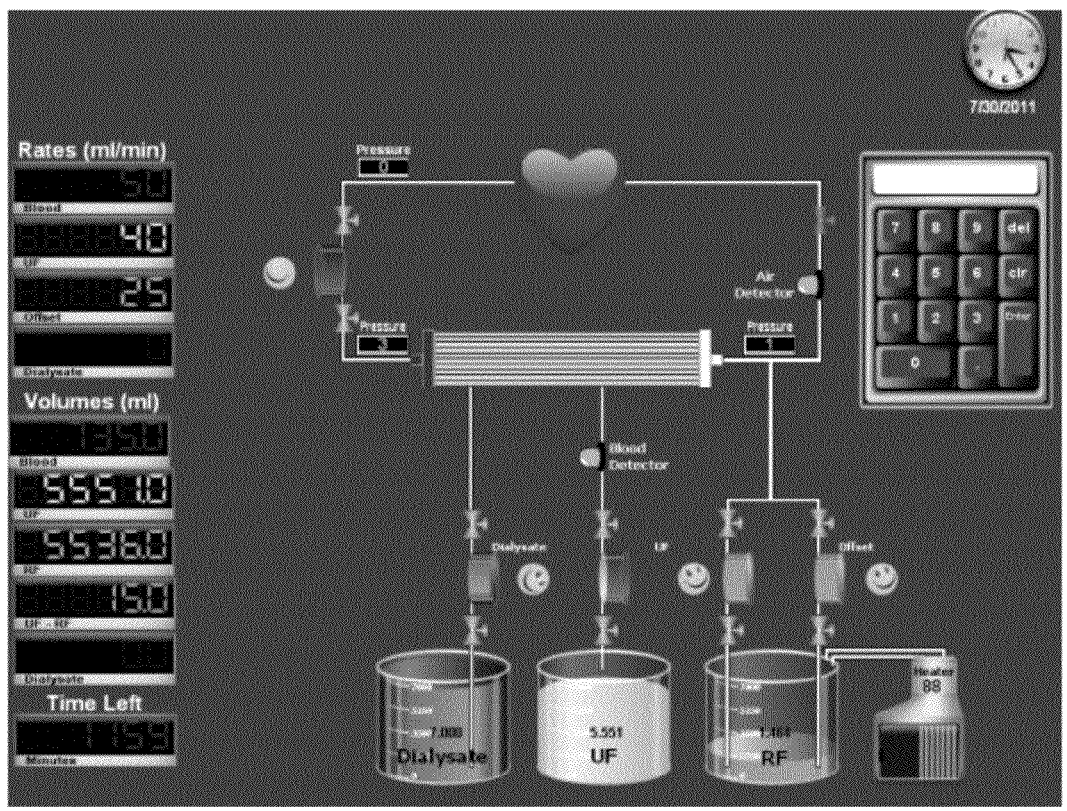
FIG. 13 is an example of a locked screen of the user interface according to some embodiments.

The accessory screens may further include a locked screen as shown in FIG. 13. This screen may display information but will not allow changes to the current therapy to unauthorized users. The screen may be by protected by a password or specific credentials. The credentials may include but are not limited to an access badge, smart card, biometric device, bar code. In order to make changes to therapy (by unlocking the screen and providing access to the main screen, for example), the user may have to enter or provide a correct password or proper credentials.

Figure 14:
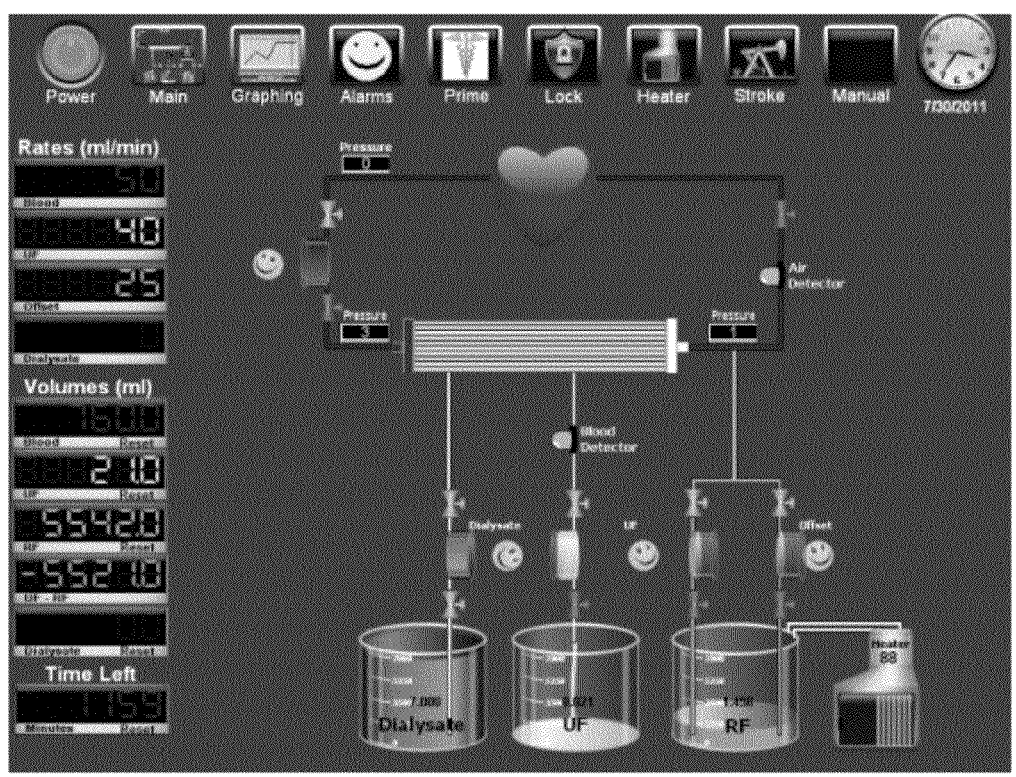
FIG. 14 is an example of a normal run screen of the user interface according to some embodiments.
Figure 16:
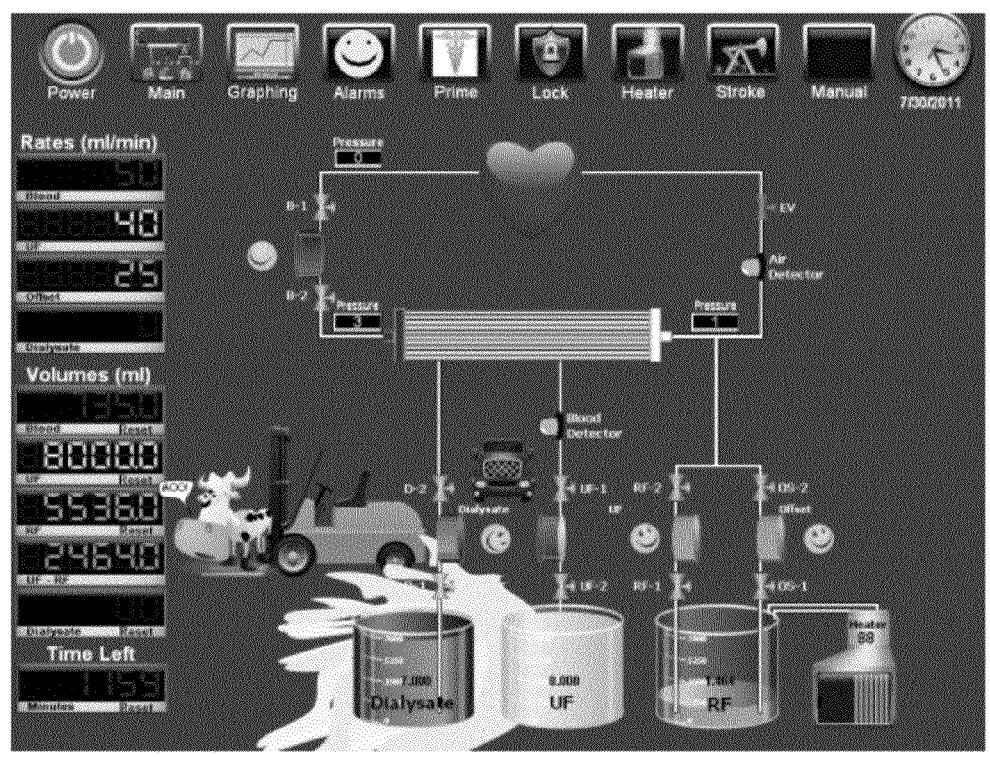
FIG. 16 is an example of an error screen of the user interface according to some embodiments.

An example of main screen for when the system is operating properly is shown in FIG. 14. An example of when there is an error, for example, with the dialysate is shown in FIG. 16.

While various embodiments of the disclosure have been described, the description is intended to be exemplary rather than limiting and it will be appeared to those of ordinary skill in the art that may more embodiments and implementations are possible that are within the scope of the disclosure.

What is claimed:

1. A fluid pump for medical fluid treatment therapies configured for small volumes of a fluid, comprising:
a first conduit configured for inflow of the fluid;
a second conduit configured for outflow of the fluid;
a fluid chamber configured to move the fluid through the pump;
a diaphragm configured to force the fluid through the fluid chamber by indirectly exerting force on the fluid chamber;
a connector configured to removably attach the pump to a motor; and
an actuator directly connected to the diaphragm, the actuator being configured to move a surface of the diaphragm,
wherein the fluid chamber includes a first surface and an opposing second surface, the first surface and the second surface defining a membrane configured to hold the fluid therebetween, at least one of the first and second surfaces includes a flexible material.

2. The fluid pump according to claim 1, wherein:
the actuator is configured to linearly move the surface of the diaphragm; and
each of the first and second surfaces includes the flexible material.

3. The fluid pump according to claim 1, further comprising:
a housing, the housing including at least a first section and a second section; and
wherein the first section includes a cavity filled with an incompressible fluid, the first conduit, the second conduit and the fluid chamber, and the cavity is disposed between the fluid chamber and the diaphragm.

4. The fluid pump according to claim 3, wherein:
the diaphragm is fixedly attached to the housing between the first section and the second section; and
the actuator is configured to move the diaphragm between a first position and a second position; the first position corresponding to when a surface of the diaphragm protrudes into the first section and the second position corresponding to when the surface of the diaphragm protrudes into the second section.

5. The fluid pump according to claim 4, wherein:
the diaphragm is configured to transfer force to the incompressible fluid when the diaphragm is in the second position, and the incompressible fluid is configured to move the fluid through the fluid chamber.

6. The fluid pump according to claim 4, wherein the second section includes a piston.

7. The fluid pump according to claim 6, wherein the first section has an extending surface and the second section has an extending surface, the extending surface of the first section facing the extending surface of the second section.

8. The fluid pump according to claim 1, further comprising:
a cap, the cap including ports configured to connect tubing to the first and second conduits.

9. A medical fluid therapy system, comprising:
at least one medical fluid pump, the pump including:
a fluid chamber configured to move a fluid through the pump;
a diaphragm configured to force the fluid through the fluid chamber by indirectly exerting force on the fluid chamber;
a plurality of valves, the valves including at least a first valve and a second valve configured to control the flow of fluid through the fluid pump;
a motor;
a controller configured to collectively control the movement of the motor and valves with respect to each other; and
an actuator directly connected to the diaphragm, the actuator being configured to move a surface of the diaphragm,
wherein the fluid chamber includes a first surface and an opposing second surface, the first surface and the second surface defining a membrane configured to hold the fluid therebetween, at least one of the first and second surfaces includes a flexible material.

10. The system according to claim 9, further comprising:
a fluid balance system,
the fluid balance system including a first pump and a second pump, each pump including the fluid chamber, the diaphragm and the first valve and the second valve,
wherein the first pump and second pump are offset of each other.

11. The system according to claim 9, further comprising:
a display, the display includes a user interface configured to enter operating parameters to control the system.

12. The system according to claim 11, wherein the user interface displays the operating status of the system.

13. The system according to claim 12, wherein the operating status includes flow rates of the fluid flowing through the pump and an angle of the valve.

14. The system according to claim 9, further comprising:
at least one pump receiving member, the at least one pump receiving member having a depression configured to receive a portion of the pump,
wherein the pump includes a housing, the housing including at least a first section and a second section,
wherein the first section has an extending surface and the second section has an extending surface, the extending surface of the first section facing the extending surface of the second section, and
wherein the depression is configured to receive the extending surface of at least the second section.

15. The system according to claim 14, further comprising:
at least first and second self-contained sections, wherein the first self-contained section includes the controller; and the second self-contained section includes the pump receiving member.

16. The system according to claim 9, wherein the system is configured for a plurality of fluid treatment modes.

17. The system according to claim 9, wherein the controller is configured to control the motor and valves based on entered volume parameters.

18. The system according to claim 17, wherein an operating status of the system is stored at predetermined intervals.

19. A disposable kit for a medical therapy system, comprising:
- a first conduit configured for inflow of a fluid;
- a second conduit configured for outflow of the fluid;
- a fluid chamber configured to move the fluid through a pump;
- a diaphragm configured to force the fluid through the fluid chamber by indirectly exerting force on the fluid chamber;
- a connector configured to removably attach the pump to a motor; and
- an actuator directly connected to the diaphragm, the actuator being configured to move a surface of the diaphragm,
- wherein the fluid chamber includes a first surface and an opposing second surface, the first surface and the second surface defining a membrane configured to hold the fluid therebetween, at least one of the first and second surfaces includes a flexible material.

20. The kit according to claim 19, further comprising:
tubing configured for the medical therapy system.

* * * * *